United States Patent [19]
Feathers, III et al.

[11] Patent Number: 5,145,642
[45] Date of Patent: Sep. 8, 1992

[54] LOAD COMPENSATED WATER FILL FOR A TABLE TOP STERILIZER

[75] Inventors: Charles H. Feathers, III, Hilton; Bhabesh K. Thakur, West Henrietta; Charles O. Hancock, Fairport, all of N.Y.

[73] Assignee: MDT Corporation, Torrance, Calif.

[21] Appl. No.: 648,901

[22] Filed: Jan. 31, 1991

[51] Int. Cl.⁵ .......................... A61L 2/00; G05D 7/00
[52] U.S. Cl. ........................................ 422/26; 422/110; 422/115; 422/116; 422/112; 422/295
[58] Field of Search ........................ 422/26, 29, 31, 33, 422/110, 112, 113, 114, 115, 116, 295

[56] References Cited

U.S. PATENT DOCUMENTS

| | | | |
|---|---|---|---|
| 4,263,258 | 4/1981 | Kalasek | 422/113 |
| 4,447,399 | 5/1984 | Runnells et al. | 422/113 |
| 4,865,814 | 9/1989 | Childress | 422/116 |
| 4,891,188 | 1/1990 | Albright et al. | 422/114 |
| 4,909,988 | 3/1990 | Childers et al. | 422/26 |

Primary Examiner—Lynn M. Kummert
Assistant Examiner—T. A. Trembley
Attorney, Agent, or Firm—Trask, Britt & Rossa

[57] ABSTRACT

In an unplumbed sterilizer, a measured quantity of liquid is introduced into a partially evacuated chamber in a dump period. The liquid quantity is automatically controlled by closing a valve in the additional conduit upon the occurrence of either (a) the chamber pressure attaining a preset value, or (b) elapsing of a preset time, whichever occurs first.

20 Claims, 4 Drawing Sheets

LOAD COMPENSATED WATER FILL FOR A TABLE TOP STERILIZER

BACKGROUND OF THE INVENTION

1. Field

This invention relates to the field of sterilizers, and more particularly relates to apparatus and methods for steam sterilizers.

2. State of the Art

Tabletop sterilizers are small pressure vessels which are typically "unplumbed," i.e., the vapor sterilant is generated from a fixed amount of liquid sterilant placed in the electrically heated vessel and vaporized therein. The liquid is admitted to the sterilizer vessel by a metering valve or shot chamber or other means, i.e. by manually dumping a measured quantity of liquid into the vessel.

The quantity of added liquid, e.g., water, must be sufficient to maintain an atmosphere of saturated vapor sterilant at the desired sterilization temperature, irrespective of the type or quantity of material comprising the load to be processed.

When materials are sterilized, the hot vapor condenses on the cold materials during the heating cycle. The condensate may be retained in the surface of the materials and not be immediately returned to the heating means. Materials such as fabrics may retain a large quantity of condensate prior to attaining the sterilizing temperature.

When the condensate is not returned to the heater, additional liquid must be added to prevent the heating surfaces from drying out. Dry heater surfaces result in a very low heat transfer rate and prevent the materials from reaching sterilization conditions in a reasonable time.

If an excessive quantity of liquid is added to the sterilizer chamber, the heating period is also prolonged and additional energy is consumed. Furthermore, additional time is often required for removing moisture from the chamber and cooling the contents upon completion of the sterilization period.

A method and means for avoiding the abovementioned problems is needed.

SUMMARY OF THE INVENTION

The invention is an improved tabletop sterilizer and a method for its operation whereby the invention ensures complete sterilization under widely varying sizes and types of loads while simultaneously simplifying the sterilization operation. The improved apparatus and method of operation of the invention overcome or minimize the aforementioned problems of previous unplumbed sterilizers.

The sterilizer of this invention includes a sterilizing chamber with an associated liquid reservoir, as is typical of unplumbed sterilizers. The chamber has the usual access door and heating means for converting liquid to vapor, e.g. water to steam. Liquid is introduced from the reservoir to an inlet to the chamber through a first conduit such as piping. A first control valve is associated with the first conduit and is operative selectively to open for a period of time, or close as needed to permit or prevent the flow of liquid from the reservoir to the chamber. A first vent conduit extends from the chamber to a drain system or the atmosphere. A second control valve is associated with the first vent conduit and is operative selectively to open or close, thereby to permit or prevent the exhaustion of air and/or vapor sterilant from the chamber.

A vacuum producing means such as a vacuum pump is connected to the sterilizing chamber for evacuating air and/or other gases therefrom. By manipulation of valves, air pumped by the vacuum pump may be directed through the chamber for cooling and drying the contents.

The pressure and temperature in the chamber is determined by sensors. The measured temperature is used to control the sterilization operation.

The operation of the sterilizer includes the steps of loading materials into the sterilizer chamber and sealing it, activating the heating means to a temperature greater than the boiling point of the sterilant-producing liquid, evacuating the chamber to a predetermined subatmospheric pressure, and opening the first control valve for a period based on the first occurring condition of (a) the sterilizer attaining a predetermined pressure higher than the evacuation pressure, or b) a fixed preset elapsed time from opening of the control valve. The first of the two conditions to occur closes the first control valve to limit the quantity of liquid introduced.

Thus, the quantity of liquid admitted to the chamber is controlled by the elapsing of a fixed time or achieving a pressure greater than the predetermined vacuum, whichever occurs first. The flow rate is a function of the liquid pressure drop, and thus a function of the sterilizer pressure.

The characteristics of the load and the temperature of the vessel determine if the fixed time is allowed to fully elapse or not. The mass, surface area, absorption capability, and thermal properties such as the rate of heat transfer are characteristics that allow for the fixed time to elapse. As the liquid enters in to the preheated vessel, which is hotter than the boiling point of the liquid, the liquid will start to vaporize. As the vapors come in contact with the load, which is cooler than the temperature of the vapors, the vapors will condense on the load. The rates at which the vapors are generated and condensed determine how much time elapses before the pressure greater than the predetermined subatmospheric pressure is achieved. A longer period for admitting liquid results in a greater quantity of liquid in the chamber.

The factors controlling the required volume of steam (and thus the liquid water) include:

(a) the actual space in the chamber which will be occupied by the steam, (b) the quantity and type of materials loaded into the chamber, and (c) the temperature of the load as well as the chamber, and (d) the water evaporation rate within the chamber.

The characteristics of the load, including mass, heat capacity, surface area, and water absorbency will affect the rate at which the evaporation exceeds condensation.

It has been discovered in practice that the relationship between loading and the required liquid volume is generally a positive function. Typically, the relationship is positive over the range of possible loadings, i.e., as the loading increases, the required water volume to prevent dryout increases.

The maximum quantity of liquid at which dryout occurs can be determined over a range of loadings for particular types of materials. This "dryout" volume of liquid must be augmented by an additional quantity of liquid to ensure the absence of dryout conditions.

In this invention, the alternative condition which closes the liquid inlet valve, e.i. first control valve, corrects for the amount of condensation occurring in the chamber, up to a maximum liquid volume. Automatic compensation is achieved for a wide range of materials, e.g. metals, fabrics, liquids, etc. and quantity of materials in the load.

DETAILED DESCRIPTION OF THE ILLUSTRATED EMBODIMENT

Figure 1:
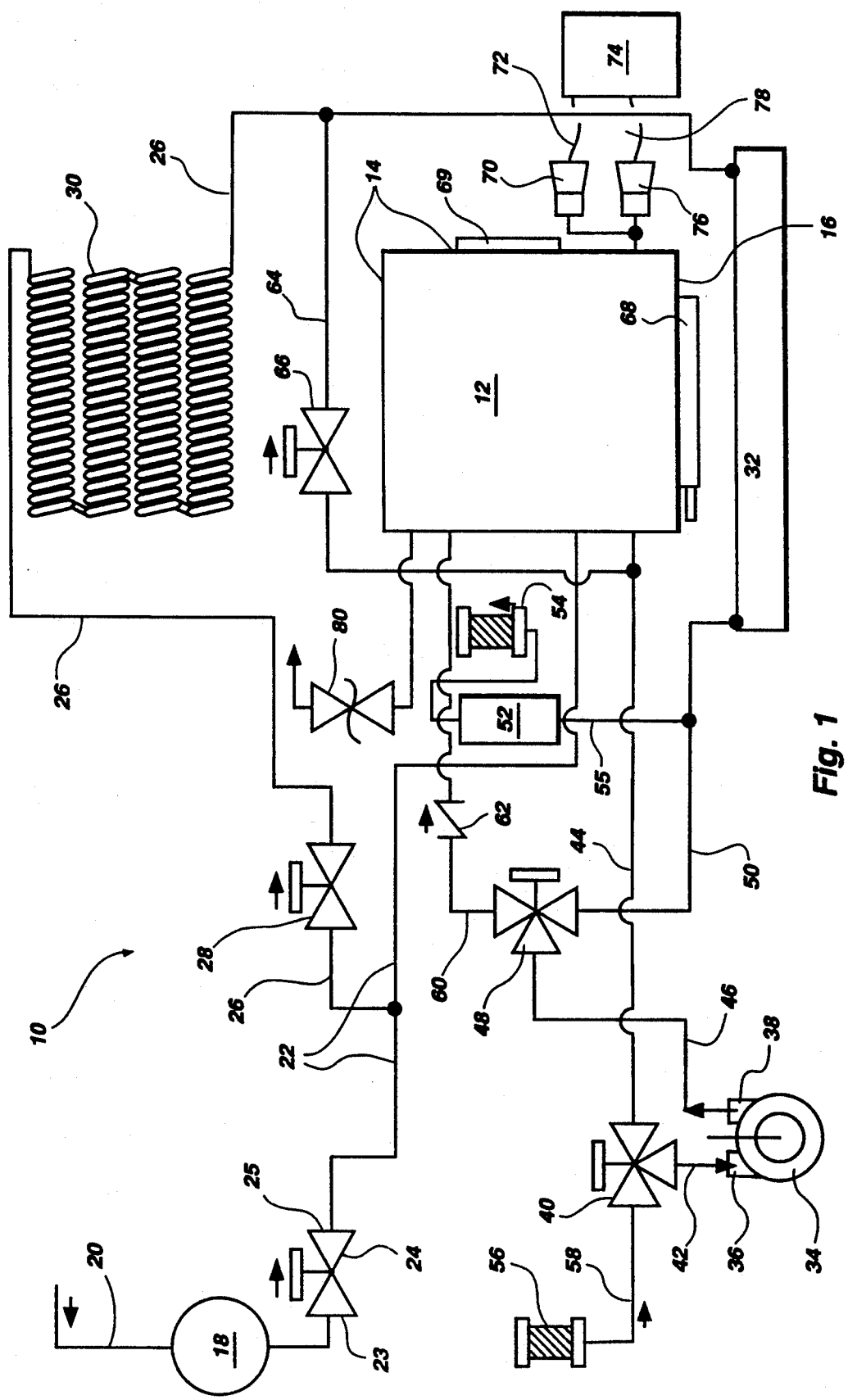
FIG. 1 is a schematic diagram of a sterilizer made and operable in accordance with the invention.

FIG. 1 depicts a tabletop sterilizer 10 made and operated in accordance with the present invention. For the purposes of this invention the term "unplumbed sterilizer" refers to a sterilizer which is not connected to any external steam source for the introduction of steam. Any steam required by sterilizer 10 will be produced by the unit itself. The sterilizer includes sterilizing chamber 12 into which materials are placed for sterilization. The chamber 12 is a pressure vessel having enclosure walls 14 including lowermost wall 16, hereinafter termed a floor. The chamber 12 is provided with a door, not shown, for closing and sealing the chamber. Sterilizer 10 is provided with a reservoir 18 for holding a quantity of a liquid 20 such as water. The reservoir 18 is connected to the chamber 12 by fill conduit 22 for passage of liquid 20 to the chamber when water fill valve 24 is open.

A vent conduit 26 with vent valve 28 is connected to fill conduit 22 or optionally directly to the chamber 12 for exhaustion of vapors therefrom. An in-line cooler 30 may be used for cooling and condensing vapors passing through conduit 26 before discharging them from the sterilizer, such as to waste reservoir 32.

Each of valves 24, 28 and 66 is shown as an electrically controlled solenoid valve in which flow is intended in one direction only. Such values are generally capable of sealingly retaining a greater pressure on the upstream, i.e. inlet side.

Valve 24 is preferably a two-way valve which is placed in a reverse direction in conduit 22 with liquid flowing into the outport 23 and out of the inport 25. Available valves useful for this application are rated for a 20 psig differential pressure from the outport 23 to the inport 25 of the valve. Therefore, the valve is capable of seeing 20 psig at the normal outport 23 with 0 psig at the normal inport 25. As pressure rises in the chamber, the normal inport 25 (now used as the outport) checks the pressure up to the rating of the valve. Therefore, a check valve normally used in conjunction with valve 24 is not needed.

A vacuum means for evacuating chamber 12 is depicted as a vacuum pump 34 having inlet port 36 and outlet port 38. Three-way valve 40 permits the inlet port 36 to be connected through conduits 42 and 44 to the chamber 12. Gases and vapors pumped from the chamber 12 by pump 34 are discharged through outlet port 38 and passed through conduit 46 to three-way outlet or exhaust valve 48 and then through conduit 50 to the atmosphere or to waste reservoir 32. An optional gas-liquid separator 52 and filter 54 may be connected to conduit 50 by conduit 55 as shown for separating and separately discharging gases from the vacuum pump 38.

Alternatively, three-way inlet valve 40 is controlled to permit the flow of air through filter 56 and conduit 58 to the inlet port 36 of the vacuum pump 34. Air discharged from the outlet port 38 of vacuum pump 34 is then passed through three-way valve 48, conduit 60 and check valve 62 to the chamber 12. Bypass conduit 64 having bypass valve 66 therein is used for venting air and vapors associated therewith to the waste reservoir 32.

A first heating element 68 is provided in or on chamber 12 for evaporating the water provided in chamber 12 into steam and for heating the steam to the desired temperature. In the particular embodiment illustrated in FIG. 1, the first heating element 68 is disposed on the outside of chamber 12 and heats the chamber floor 16. Thus, liquid introduced through fill conduit 22 as well as vapors which condense on the cooler materials are directed to the floor for reheating and vaporization. Alternatively, heating element 68 may be placed inside chamber 12. In either case, the sterilizer chamber floor 16 and heating element 68 act as a heat sink to store thermal energy. In addition, the inside surface of floor 16 is a heat transfer surface for heating and evaporating the liquid. A second heating element 69 is associated with the sterilizer for controllably heating the walls 14. The first heating element 68 and second heating element 69 may preferably be heated by connection to a source of electricity.

A temperature sensor 70 monitors the temperature in chamber 12 and transmits the information by wire 72 to microprocessor control unit 74. Likewise, the pressure within chamber 12 is sensed by pressure sensor 76 and transmitted to control unit 74 by wire 78. Microprocessor control unit 74 includes programs for controlling the operation of valves 24, 28, 40, 48 and 66, vacuum pump 34 and heating elements 68 and 69 to achieve a timed cycle which ensures sterilization of materials in the chamber 12.

Different combinations of sterilization time and temperature are pre-programmed in the control unit to accommodate differing materials. Thus, a flash sterilization of wrapped metal instruments may be programmed for 3-10 minutes of exposure to steam at 132° C. (270° F.), at which the saturation pressure is 41.9 psia. A standard sterilization of non-liquid materials may be programmed for 30 minutes of exposure to steam at 121° C. (250° F.), at which temperature the saturation pressure is 29.8 psia. Sterilization of liquid materials in small containers may be programmed for 30 minutes of exposure to steam at 132° C. (270° F.).

A safety relief valve 80 and other appurtenances not shown may be included in the apparatus as practiced in the art.

Figure 2:
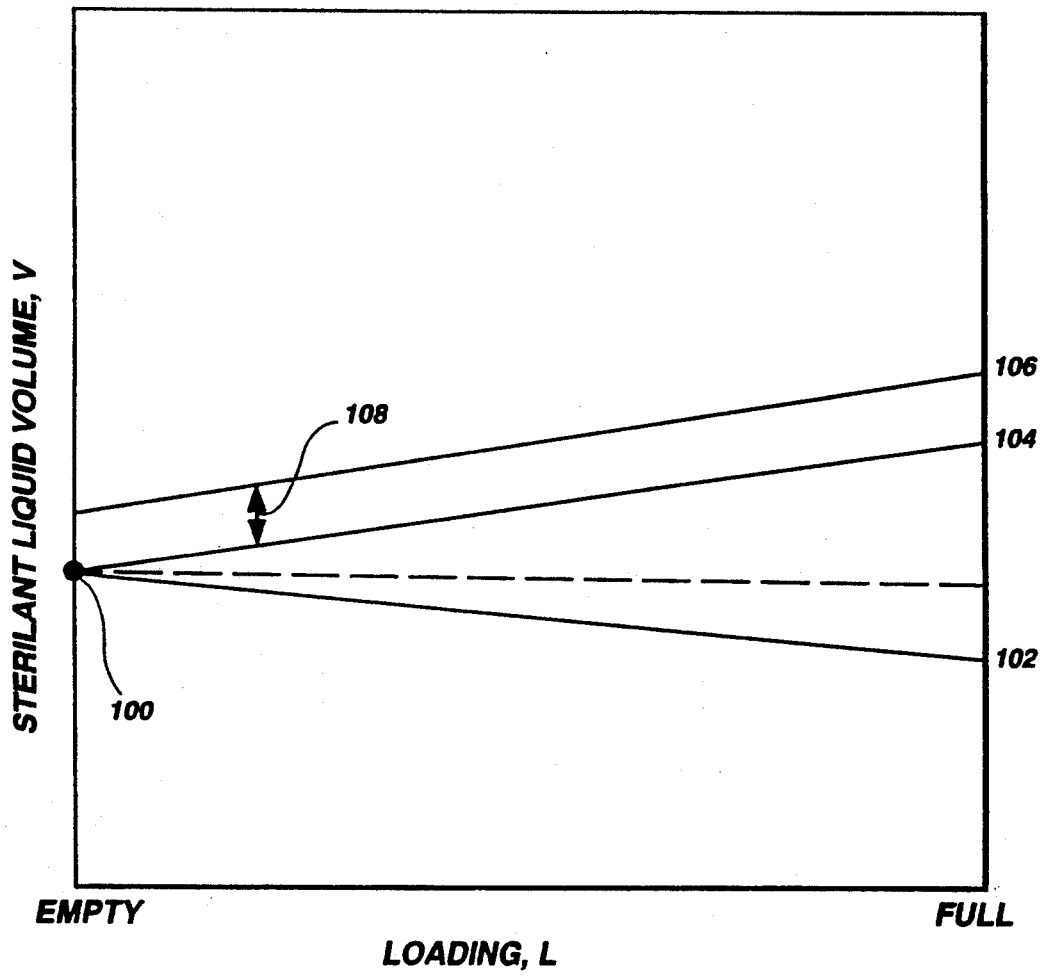
FIG. 2 is a generalized graphical depiction of the relationship between sterilizer loading and dryout liquid volume.

In conducting a sterilization procedure, the materials placed in the chamber are colder or cooler than the desired sterilization temperature, and the vapor will condense on and in the materials. A considerable quantity of the condensate remains associated with the materials and does not return to the heating means. It comprises a reservoir of liquid not available to the heating means for revaporization. The heater surfaces may actually dry out. Thus, the actual liquid requirement increases rather than decreases, as the loading increases. The relationship of loading and the required liquid sterilant volume is illustrated on the generalized graphical plot of FIG. 2. In this graph, the ordinate axis represents the volume V of sterilant liquid, and the abscissa represents the loading L which may be expressed, for example, as mass of materials per unit volume in the sterilizer chamber. The loading L is shown as varying from an empty chamber to a nominally "full" chamber, i.e. the recommended maximum load.

Point 100 is the liquid water volume which may be evaporated to completely fill the chamber with saturated steam at the desired sterilization temperature, there being no excess for wetting the heaters, etc. This is the "dry-out" volume for the empty chamber.

Curve 102 shows the theoretical liquid water volume which, when evaporated, will completely occupy the remaining space of the chamber at the loading level. In actual practice, condensation and retention of steam during the heating period increases the "dryout" water to that of curve 104. Thus, the relationship of required liquid volume V to loading L is a positive function.

In actuality, a slight excess of liquid is desirable to maintain liquid contact with the heating means surface and prevent dryout during the heating and sterilization periods. As shown in curve 106, this additional liquid volume 108 may be determined as a percentage of the dryout volume, or it may be a constant additional volume over and above the dryout volume, for example. In any case, it must be sufficient to maintain a liquid phase on the heating surface for maintaining a high vaporization rate. However, its volume must not be so great as to significantly slow the overall heating rate or lengthen subsequent venting and cooling operations.

Curve 104 is not necessarily a straight line, since the relationship is not necessarily linear. However, the measured chamber pressure is a direct function of the condensation occurring in the chamber, so the shape of curve 104 has little effect upon the controlled liquid volume introduced to the chamber.

The liquid volume tied up as non-returned condensate during the heat-up depends upon the particular materials. Nevertheless, the time required to attain the predetermined chamber pressure is directly related to the required volume of liquid sterilant, e.g., steam, over a wide range of loading, rather than tied to a particular type of material.

In this invention, the sterilizer controller microprocessor is programmed to open the fill valve 24 following a pre-sterilization evacuation step.

Open fill valve 24 allows liquid sterilant such as water to be drawn into the chamber 12 at a rate which decreases with time. This decreased rate occurs because some of the liquid drawn into the chamber is immediately evaporated, raising the pressure in the chamber. A constriction may be placed in the liquid conduit to control the flow rate.

Fill valve 24 is then programmed to be closed when one of the two conditions occurs:

(a) when a preset pressure greater than the evacuation subatmospheric pressure is attained in the sterilizer chamber, or (b) when a preset time from the opening of the fill valve 24 has elapsed.

The following factors are interrelated: (a) sterilizer chamber size and heat capacity, (b) flow characteristics of fill valve 24 and associated conduit, (c) heating capacity of heaters in the chamber, (d) the final pre-evacuation pressure in the chamber, (e) preset pressure for closing fill valve 24, and (f) preset time to close fill valve 24. Factors (e) and (f) are controllable so that for a given sterilizer, single values of the preset pressure and preset time will provide sufficient liquid to prevent either dryout or an excess of liquid.

Figure 3:
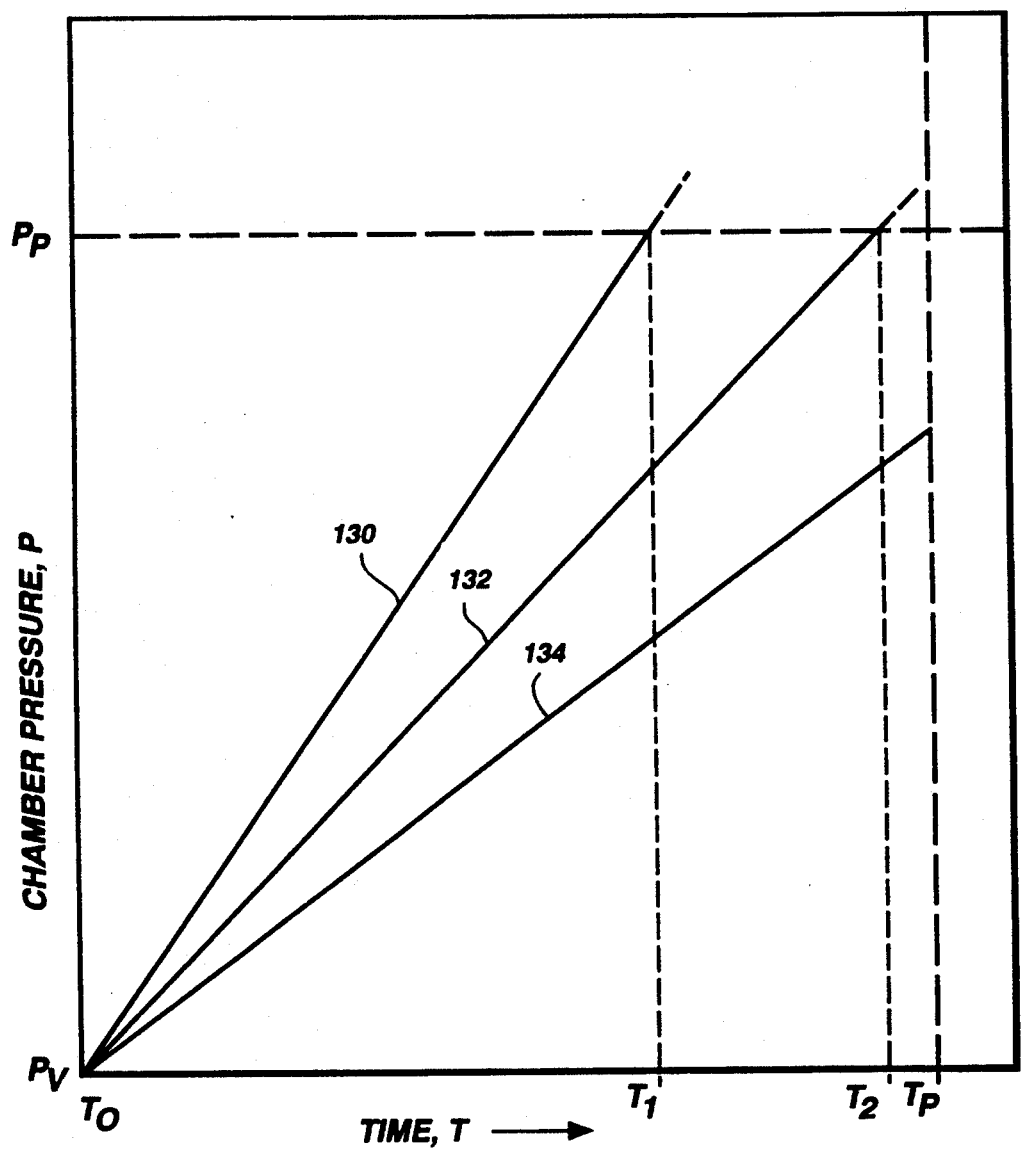
FIG. 3 is a generalized graphical depiction of the control scheme for controlling the volume of liquid sterilant based on alternative preset values of chamber pressure and time.

FIG. 3 is a generalized representation of how the invention operates to control the volume of liquid sterilant introduced into the sterilization chamber.

Following an initial evacuation step to a particular chamber subatmospheric pressure, the fill valve 24 is opened for a controlled time period to permit sterilant liquid, e.g. water which will be vaporized into steam, to flow into the chamber 12. The liquid is drawn into the chamber by the vacuum. The quantity of liquid introduced is a direct function of the time T that fill valve 24 is open.

As shown in FIG. 3, fill valve 24 is opened at time $T_0$, at which time the pressure $P_v$ in the chamber is at a predetermined subatmospheric value such as $-7$ psig.

Preset values of chamber pressure P and time T are entered into the sterilizer controller 74 such that the fill valve 24 will be automatically closed upon the occurrence of either of two events, whichever occurs first.

One of the events is the attainment of a preset chamber pressure $P_p$ such as, for example, any preset pressure value between $P_v$ and atmospheric pressure. The other event is the elapsing of preset time $T_p$ such as e.g. 22 seconds. The occurrence of either of these events will result in the end of the liquid dump phase of the sterilization cycle.

In FIG. 3, $T_I$ represents the dump time which provides the optimum liquid volume for a sterilization chamber. Curve 130 represents the pressure increase as a function of time. Preset pressure $P_p$ is attained at time $T_1$, before preset time $T_p$ is elapsed and the dump cycle is completed at time $T_1$.

Curve 132 illustrates the pressure rise for a partially loaded chamber. Preset pressure Pp is reached at time T2, at which time the fill valve 24 is closed. A greater liquid volume is introduced into the chamber than in curve 130, because of the increased dump time.

Curve 134 illustrates the pressure rise for a highly loaded chamber. The pressure rise is slower because of greater condensation and moisture retention in the materials. In this case the preset time $T_p$ elapses before the preset pressure $P_p$ is attained. The valve 24 is closed at time $T_p$, which provides the maximum liquid volume under all loading conditions. Increasing the loading beyond that of curve 134 does not result in a greater liquid volume.

Thus, the variable liquid volume having an absolute maximum is provided for the sterilizer. The variable volume is an indirect function of the net rate of heatup in the chamber, irrespective of the type of materials or the total load.

For any particular sterilizer system, the desired preset values are dependent upon the physical characteristics of the hardware and the desired sterilization temperature. Once the correct preset values are entered into the controller, further adjustments are not required for sterilizing different materials.

The relationship of required liquid volume to loading may be determined experimentally for a given sterilizer with various classes of materials. However, the relationship is such that regardless of the type of material, single preset values of pressure and time will achieve the desired liquid volume over a wide range of loading and material types. These preset functions are programmed in the sterilizer controller microprocessor for automatic use with the particular sterilizing cycle used for each type of material.

Figure 4:
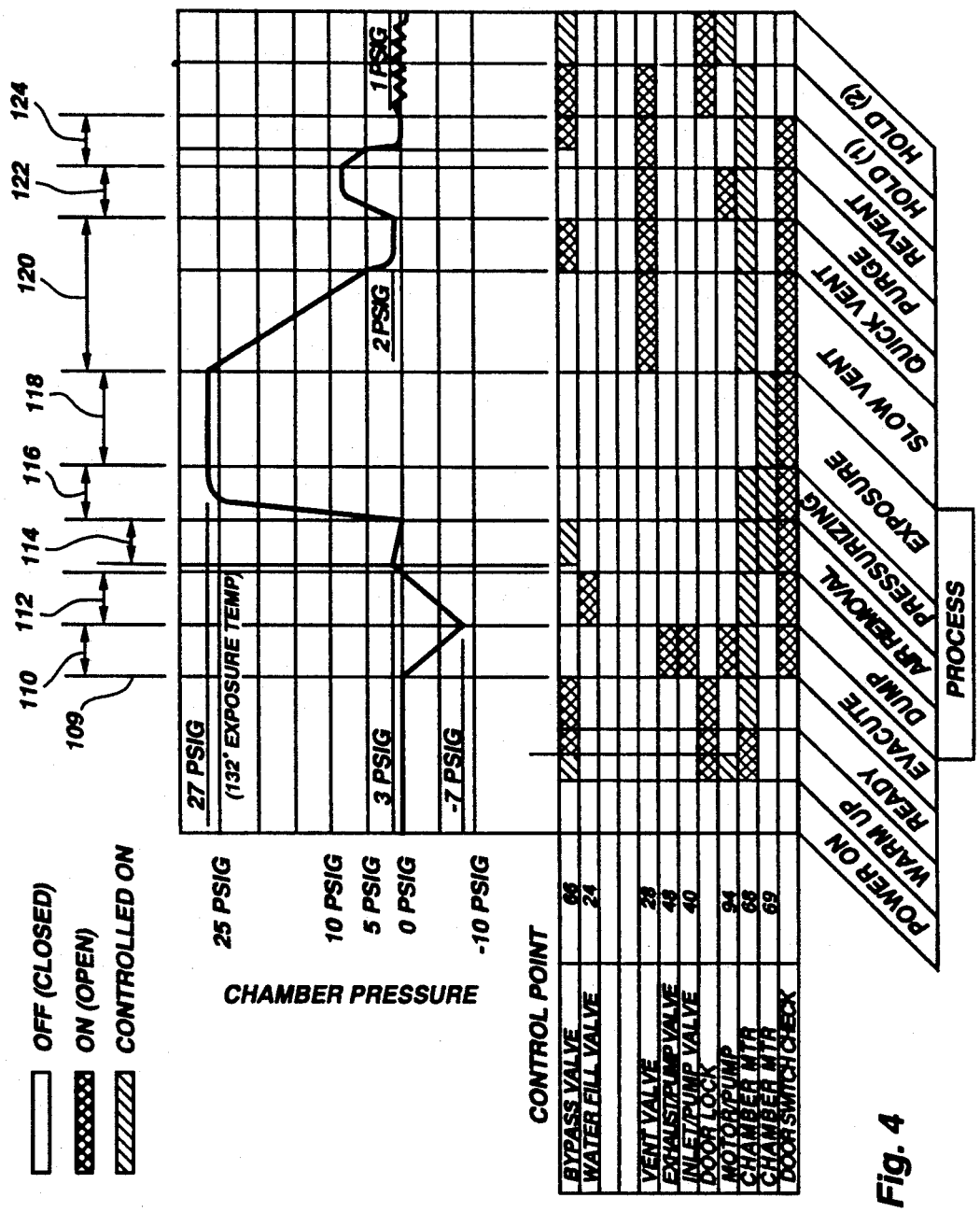
FIG. 4 is a sequence timeline indicating the process steps for an exemplary complete sterilization cycle, in accordance with the invention.

Each of the steps in an exemplary sterilization cycle is illustrated in FIG. 4. The sterilization temperature shown is 132° C. (270° F.), at which temperature the water saturation pressure is about 27 psig. The numbers of the control points correspond to the particular valves, pump, heaters, etc. of FIG. 1. The cycle is started with materials placed in the sterilizer chamber as desired.

The power is turned on to activate the sterilizer components, including the computerized microprocessor control unit 74. The chamber door is closed and locked. The following steps are automatically controlled by the microprocessor controller 74 on a timed or other basis. Manual controls are provided where desired to override the automatic control mode.

Heater 68 is turned on to begin heating the chamber 12 and associated heat sink. With bypass valve 66 open, the vacuum pump 34 is turned on for a short timed period to pump air through conduit 46, valve 48 and conduit 60 to the chamber 12. The air purges gases and vapors from the sterilizer chamber through conduit 64 and valve 66 to the waste reservoir.

At the end of a timed period, the vacuum pump 34 is turned off. Chamber heater 68 continues to operate and maintains a preset temperature higher than the atmospheric boiling point of the sterilant liquid 20. An exception to this rule is made when liquids are to be sterilized. A preset temperature slightly below the boiling point is then used. Typically, a preset temperature of 90° C. (194° F.) is used with aqueous liquids.

At controlled time 109 an evacuation step is begun. Bypass valve 66 is closed. Valves 40 and 48 are set to permit evacuation of the sterilizer chamber 12, and the vacuum pump 34 is turned on to evacuate the chamber to a predetermined subatmospheric pressure, here shown as −7 psig, i.e, 7.7 psia.

Following evacuation, valves 40 and 48 are closed to the chamber 12, and fill valve 24 is opened for a controlled dump time 112 to permit liquid to flow from reservoir 18 to the chamber. The dump time 112 is completed when either the preset pressure is attained, or a preset dump time is reached, whichever occurs first. The dump time 112 provides the necessary quantity of liquid, e.g. water, to the chamber 12 to prevent dryout of the heating surfaces. Vaporization of the liquid during the dump period is shown as increasing the chamber pressure to a preset pressure of atmospheric pressure, which closes the water fill valve 24.

Following the liquid dump, bypass valve 66 is opened to permit additional air removal and pressure equalization. This air removal period 114 may be based on time or chamber pressure. At the beginning of this period, typically lasting about one minute, chamber heater 69 is turned on to heat the chamber walls and assist heater 68 in vaporizing the sterilant liquid. The quantity of liquid added in the dump period must be sufficient to offset that lost as steam in this air removal step.

Bypass valve 66 is then closed and heating is continued in time period 116 to bring the chamber temperature and pressure to the desired conditions. Upon attaining the desired sterilization conditions, one of the heaters, e.g. heater 69, is shut off and a sterilization exposure period 118 is begun. The sterilization period 118 is dependent upon the particular materials to be sterilized, and may be, for example, 3 or 10 minutes in length at 132° C. Sterilization for 3 minutes is considered a "flash" sterilization. Temperature-sensitive materials are conventionally sterilized at 121° C. for a period of 30 minutes. The sterilization temperature and/or time may be varied depending on the type of materials and other factors.

Following the sterilization period 118, vent valve 28 is partially opened and the chamber slowly vented for a period 120 until a preset pressure, e.g., 5 psig is attained. Valve 28 is then further opened to quickly vent the remaining gases. The vapors are condensed in cooler 30 and discharged.

The chamber is then purged with air from vacuum pump 34 for a time period 122 to cool the chamber contents. The excess pressure in the chamber is then relieved by a revent step 124.

This system provides unique advantages in an unplumbed sterilizer.

In this invention, an adequate liquid volume is introduced to the chamber to prevent dryout, regardless of the quantity or type of materials loaded in the chamber.

The required volume of water or other liquid may be predetermined for each model of sterilizer. The preset time and preset pressure are entered into the microprocessor controller. Thus, the correct liquid volume is introduced automatically in response to a system microprocessor controller.

The addition of large excesses of liquid is avoided. Such excess volumes result in heating rates which are undesirably low.

In addition, the inconvenience of manually measuring and dumping a calculated liquid volume is avoided. The reservoir may be made of sufficient size to hold sufficient liquid for multiple cycles. It may even be automated to be filled semi-continuously to a given level, if desired.

A shot chamber or metering valve is not required, greatly simplifying the sterilizer as well as the operating procedure.

Use of the invention provides more precise control over the sterilization process. Dryout as well as overdosing will not occur; the repeating of aborted cycles is avoided, and operation of the sterilization cycle is simplified.

By using this system, the overall cycle time is typically shortened, enabling additional sterilization cycles to be performed in a given time period.

In one embodiment, a check valve in the water dump line is made unnecessary, because the control valve, when reversed, is capable of handling pressure which is exerted from only one direction.

Reference herein to details of the illustrated embodiments is not intended to restrict the scope of the appended claims which themselves recite those features which are regarded as important to the invention.

What is claimed is:

1. A method for producing a vaporized sterilant from a liquid in a sterilizer, aid method comprising:
   providing a sterilizer having a chamber with walls and floor, said floor having controllably heatable heat sink structure associated therewith having a heat transfer surface for heating and vaporizing a liquid sterilant;

heating said sink structure to a temperature exceeding the boiling point of said liquid sterilant;

evacuating said chamber for a time to attain a predetermined subatmospheric pressure within said chamber;

introducing into said chamber a quantity of liquid sterilant by opening a valve to said chamber over a time period, said time period being terminated upon the first occurring of alternative conditions, said alternative conditions being (a) said sterilizer pressure obtaining a predetermined value higher than said predetermined subatmospheric pressure and (b) expiration of a preset elapsed time from said expiration of a preset elapsed time from said opening of said valve; and controllably continuing heating said heat sink structure to produce a vaporized sterilant atmosphere at a predetermined sterilizing temperature for a controlled sterilization time period.

2. The method of claim 1, wherein said heat transfer surface is positioned in a lowermost portion within said chamber.

3. The method of claim 1, wherein said heat transfer surface comprises the interior floor surface of said chamber and said heat sink structure comprises the floor material thereof.

4. The method of claim 1, wherein said heat sink structure is heated by electrical heating means.

5. The method of claim 1, comprising the further step of controllably heating the walls of said chamber to maintain said sterilizing temperature therein.

6. The method of claim 1, comprising the further steps of venting said vaporized sterilant from said chamber and cooling said chamber following said sterilization at said predetermined sterilizing temperature for said time period.

7. The method of claim 1, wherein the rate of introducing said liquid sterilant to said chamber is a known function of said chamber pressure.

8. The method of claim 1, wherein said liquid sterilant includes water and said vaporized sterilant includes saturated steam.

9. The method of claim 1, wherein said subatmospheric pressure is between 5 and 12 psia.

10. The method of claim 1, wherein said quantity of introduced liquid sterilant is controlled to be less than a preset maximum quantity.

11. An improvement in a tabletop sterilizer of the type having a sterilizing chamber, liquid reservoir structure connected by a first conduit means to said chamber for introducing liquid thereto, heating means associated with said chamber for heating and evaporating said liquid to a vapor sterilant, vacuum producing means for evacuating said chamber, pressure sensor and temperature sensor means for measuring said pressure and temperature within said chamber and producing output signals, first control valve means in said first conduit means to selectively open and close said first conduit means to liquid flow therethrough, the improvement comprising:

timer means for shutting said first control valve means when a preset time has elapsed; and controller means receiving output signals from said pressure and temperature sensors and said timer means, said controller means being structured for shutting of said first control valve means upon the first occurring of alternative conditions, said alternative conditions being (a) said sterilizer pressure attaining a predetermined value higher than a predetermined evacuation pressure and (b) expiration of a preset elapsed time from said opening of said first control valve.

12. The improvement of claim 11, wherein said rate of introducing said liquid is a predetermined function of said pressure in said chamber.

13. The improvement of claim 11, further comprising: vent means for venting gaseous contents including said vapor sterilant from said chamber following sterilization of materials.

14. The improvement of claim 11, wherein said vacuum producing means comprises a vacuum pump.

15. The improvement of claim 14, further comprising: cooling means for introducing cool gas stream into said chamber while venting.

16. The improvement of claim 15, wherein said cooling means comprises air conduit means for introducing air from the outlet of said vacuum producing means to said chamber for passage therethrough.

17. The improvement of claim 11, further comprising: a constriction in said first conduit means to limit the flow rate of liquid passing therethrough.

18. The improvement of claim 11 further comprising control means limiting said time between said opening and said closing of said first control valve means to a preset maximum.

19. The improvement of claim 11, wherein said first control valve means is a solenoid valve reversed to have its inlet end on the downstream side thereof.

20. A tabletop sterilizer for sterilizing materials, comprising:

sterilizing chamber means having walls and floor, and being sealable from the atmosphere;

heatable heat sink means associated with said floor for vaporizing a liquid to a vapor sterilant;

heating means to heat said heatable heat sink means;

vacuum producing means communicating with said sterilizing chamber means for evacuation thereof to a predetermined subatmospheric pressure;

reservoir means for retaining a liquid therein;

first conduit means for passing said liquid from said reservoir means to said sterilizing chamber means;

on-off valve means in said first conduit means for timedly controlling passage of said liquid therethrough;

timer means for limiting the actual liquid passage time to a preset value;

pressure sensor means positioned to sense the pressure within said sterilizing chamber means;

temperature sensor means positioned to sense the temperature within said chamber means; and controller means to activate said vacuum producing means, to activate said on-off valve means for controlling said passage of said liquid to said sterilizing chamber means, and to control said heating means to maintain a predetermined sterilization by said vapor sterilant for a predetermined time and temperature;

wherein said on-off valve means is turned off at the first occurring condition of (a) said sterilizer pressure attaining a predetermined value higher than said predetermined subatmospheric pressure and (b) expiration of said preset value of said liquid passage time.

* * * * *